United States Patent [19]

Fauvarque et al.

[11] Patent Number: 5,155,232
[45] Date of Patent: Oct. 13, 1992

[54] ORGANIC MATERIAL FOR NON-LINEAR OPTICS

[75] Inventors: Jean-Francois Fauvarque, Paris; Victorien Ratovelomanana, Thiais; Anny Jutand; Christian Amatore, both of Paris, all of France

[73] Assignee: Alcatel N.V., Amsterdam, Netherlands

[21] Appl. No.: 474,713

[22] PCT Filed: Jul. 20, 1989

[86] PCT No.: PCT/FR89/00382
§ 371 Date: Apr. 2, 1990
§ 102(e) Date: Apr. 2, 1990

[87] PCT Pub. No.: WO90/01724
PCT Pub. Date: Feb. 22, 1990

[30] Foreign Application Priority Data
Aug. 1, 1988 [FR] France .................. 88 10373

[51] Int. Cl.$^5$ .................. C07D 303/12; C07D 307/38
[52] U.S. Cl. ...................... 549/74; 519/491; 519/479; 519/480; 519/72; 548/530; 548/558; 548/561; 549/68
[58] Field of Search ............ 519/72, 68, 65, 491, 519/479, 480; 548/550, 558, 561; 549/74

[56] References Cited
U.S. PATENT DOCUMENTS
4,174,405 11/1979 Relyea et al. .................. 549/65
4,863,503 9/1989 Anthony et al. ................ 549/72

FOREIGN PATENT DOCUMENTS
220042  4/1987 European Pat. Off. .......... 549/491
145103 11/1980 German Democratic Rep. ................................. 549/491
96639 10/1986 Japan ............................... 549/491
1199754 12/1985 U.S.S.R. ........................... 549/491

OTHER PUBLICATIONS
Marowsky et al., *J. Opt. Soc. Am B*, "Efficiency studies of second-harmonic-active organic dye coverages," 4(6), pp. 956–961 (1987).

Primary Examiner—Richard L. Raymond
Assistant Examiner—Mark W. Russell
Attorney, Agent, or Firm—Brunell & May

[57] ABSTRACT

An organic material for non-linear optics comprising:
an electron donor group constituted by a heteroaromatic cycle;
an electron attractor group selected from $NO_2$ and CN; and
an electron effect transmitter group selected from an aromatic system of the phenyl ring type, or a chain having n atoms of carbon including a double or a triple bond (n<4).

8 Claims, No Drawings

ORGANIC MATERIAL FOR NON-LINEAR OPTICS

The present invention relates to an organic material for non-linear optics.

Materials having non-linear properties in optics may be used for numerous applications: frequency doublers; optical bistables; switches; modulators; directional couplers; parametric amplifiers; etc.

A small number of inorganic materials which are non-isotropic, and in particular non-centrosymmetrical, are known which possess a non-zero second order coefficient and non-linear optical properties. These include in particular potassium-dihydrogen-phosphate (KDP), and lithium niobate and tantalate (LiNbO$_3$, LiTaO$_3$, ... ).

It is often difficult to make these inorganic materials. That is why interest has been shown in organic materials having non-linear properties, in particular when the materials are polymers, thermoplastic, or film-forming.

Optical non-linearity is generally obtained by incorporating highly hyperpolarizable polar molecules or groups of molecules in the organic material by mixing or by chemical grafting.

Such molecules are synthesized by associating an electron attractor group with an electron donor group via a group for transmitting electron effects.

For example, the following materials are known:

paranitroaniline (PAN)

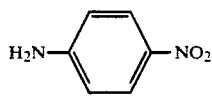

N (nitro 4 phenyl) N methyl amino 2 acetonitrile (NPAN)

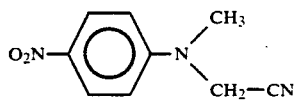

dinitro 2-4 phenyl L alanine (MAP)

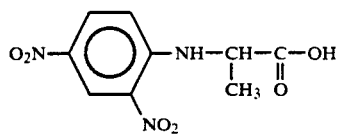

methyl 3 nitro 4 pyridine N-oxide (POM)

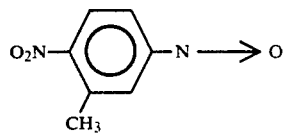

These molecules are characterized by their coefficient of hyperpolarizability $\beta$ defined by the series development of the dipolar moment $\vec{\mu}$ as a function of the electric field E $$\vec{\mu} = \vec{\mu}_o + \alpha \vec{E} + \beta |\vec{E}|^2 + \ldots$$

The coefficient $\beta$ may be measured by the EFISH method (Electric Field Induced Second Harmonic generation).

Many authors judge the value of a synthesized molecule on the basis of the value of its molecular hyperpolarizability associated with infrared frequency doubling.

For these applications, molecules having a large number of atoms may be suitable, however experience shows that such molecules absorb light strongly in the visible spectrum and this may be unacceptable. For electro-optical applications, the useful magnitude is rather hyperpolarizability per unit mass or per unit volume.

The object of the present invention is to find molecules having all the essential parts (attractor group, donor group, and transmitter group) using as small a number of atoms as possible, while nevertheless conserving a good value of constant field molecular hyperpolarizability.

The present invention provides an organic material for non-linear optics comprising an electron attractor group and an electron donor group interconnected by an electron effect transmitter group, the material being characterized by the fact that:

the electron donor group comprises an aromatic heterocycle in the form of a 5 member ring that includes a heteroatom selected from S, O, and N;

the electron attractor group is selected from NO$_2$ and CN; and the transmitter group is selected from the group consisting of carbon chains having n atoms of carbon (where n<4) and including a double or a triple bond, and an aromatic system such as a phenyl ring.

The nitrogen atom may be bonded to a radical R selected from H, CH$_3$, and C$_2$H$_5$.

In a first variant, the said transmitter group is constituted by an ethenyl bond.

By way of example, the material of the invention may satisfy one of the following formulas:

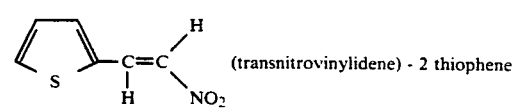

(transnitrovinylidene) - 2 thiophene

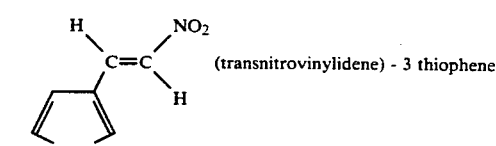

(transnitrovinylidene) - 3 thiophene

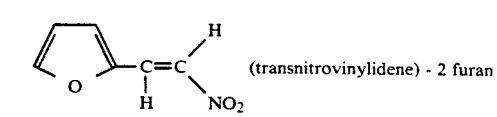

(transnitrovinylidene) - 2 furan

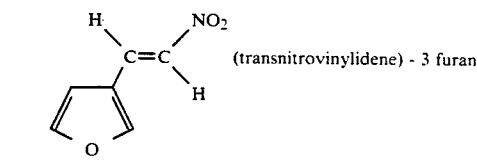

(transnitrovinylidene) - 3 furan

-continued

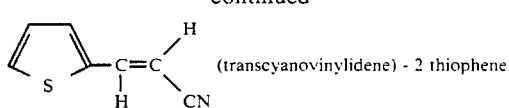
(transcyanovinylidene) - 2 thiophene

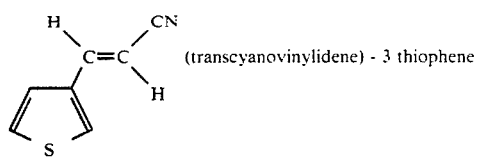
(transcyanovinylidene) - 3 thiophene

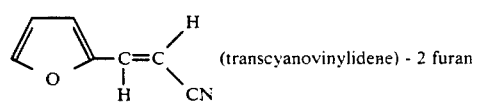
(transcyanovinylidene) - 2 furan

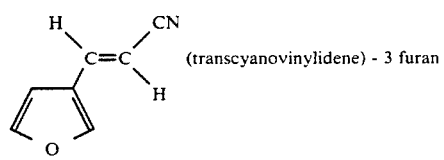
(transcyanovinylidene) - 3 furan

In a second variant, the said transmitter group is constituted by a phenyl ring. The material of the invention may then satisfy one of the following formulas:

(cyano 4 phenyl) - 2 furan (cyano 4 phenyl) - 2 thiophene (nitro 4 phenyl) -2 furan (nitro 4 phenyl) - 2 thiophene In another variant, the said heteroaromatic cycle is substituted at 5 by a group selected from $CH_3O$, $CH_3S$, $NH_2$, $CH_3NH$, $(CH_3)_2N$.

In all molecules of the invention, the electron donor characteristic and the aromatic characteristic are concentrated on a smaller number of atoms than in prior art molecules since they contain aromatic cycles which are rich in electrons (substituted or non-substituted furan, thiophene, or pyrrole).

With these molecules possessing a small number of atoms, it is possible to achieve high molecular hyperpolarizability at zero frequency.

Excellent results may be obtained by using the cyano group (—CN) which is smaller than the nitro group (—$NO_2$).

The present invention also provides methods of synthesizing the above materials.

Other characteristics and advantages of the present invention appear from the following description of embodiments given by way of non-limiting illustration.

EXAMPLE 1

(Transnitrovinylidene) - 2 thiophene was prepared:

In a 250 $cm^3$ three-necked Wolff bottle fitted with a thermometer, a dropping funnel, and a septum, the following were placed: 5.60 grams (g) of thiophene - 2 carbaldehyde; 3.55 g of nitromethane; 1.01 g of Aliquat 336 (Aldrich); and 100 ml of methanol. The mixture was cooled to about 0° C. to 5° C.

Under magnetic stirring, 10 ml of 10N caustic soda were added drop-by-drop using the 10 ml dropping funnel while ensuring that the temperature did not rise above 5° C.

Stirring was continued for 10 minutes after all the soda had been added. Then the entire mixture was transferred drop-by-drop into 50 ml of a solution of 4N hydrochloric acid.

The mixture was then stored at 4° C. for 24 hours. Crystals were formed which were filtered and washed in distilled water and then dried for 36 hours.

This provided 6.9 g of product, i.e. a yield of 89%. The product was then purified by filtering on silica.

EXAMPLE 2

(Transnitrovinylidene) - 3 thiophene was prepared.

The above procedure was performed using 5.4 g of thiophene - 3 carbaldehyde. 6.6 g of product were obtained, i.e. a yield of 85%.

EXAMPLE 3

(Transnitrovinylidene) - 2 furan was prepared

The above procedure was applied to 4.8 g of furfuraldehyde. 5.02 g of product were obtained, i.e. a yield of 72%.

EXAMPLE 4

(Transnitrovinylidene) - 3 furan was prepared

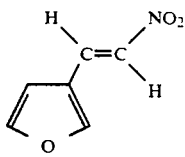

The above procedure was applied to 4.8 g of furan -3 carbaldehyde. 5.7 g of product were obtained, i.e. a yield of 82%.

The four materials analogous to the above four materials but in which the nitro group is replaced by a cyano group may be prepared in similar manner.

EXAMPLE 5

(Cyano 4 phenyl) - 2 furan was prepared

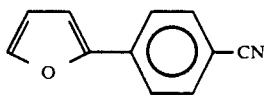

Since bromo-2-furan is not commercially available, the corresponding zinc derivative was prepared by treating 5 m.moles of furan with 6 m.moles of butyllithium in 50 ml of tetrahydrofuran (THF). The resulting solution was then added to a solution of 6 m.moles of zinc chloride $ZnCl_2$ in 60 ml of THF. The resulting zinc compound was then made to react on 5 m.moles of parabromobenzonitrile in the presence of the palladium complex $Pd[P(C_6H_5)_3]_4$. (Cyano 4 phenyl) - 2 furan was obtained with a yield of 74% of isolated product.

The absorption of this material was at a maximum at 304 nanometers, with its molecular absorption coefficient $\epsilon$ then being 48,740. This coefficient was close to 0 at 400 nanometers. Its optical transparency was perfect in the frequency range of the visible spectrum and the near infrared. It may therefore be used for generating a second harmonic in the blue region of the visible spectrum using a laser in the infrared or the near infrared.

EXAMPLE 6

(Cyano 4 phenyl) - 2 thiophene was prepared

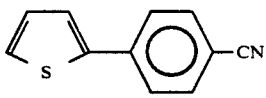

This was done by preparing the magnesium derivative of bromo 2 thiophene (5 m.moles) in 50 ml of THF. The magnesium derivative was caused to react with paraiodobenzonitrile in the presence of the palladium complex $Pd[P(C_6H_5)_3]_4$.

(Cyano 4 - phenyl) - 2 thiophene was obtained with a yield of 73% for the isolated product.

This material had an absorption maximum at 302 nanometers, where its molecular absorption coefficient $\epsilon$ was 87,623. This coefficient was closed to 0 at 400 nanometers. It has the same advantages of the product of Example 5.

EXAMPLE 7

(Nitro 4 phenyl) - 2 furan may be obtained in analogous manner from

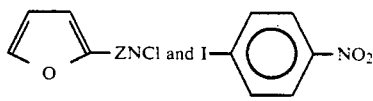

Its absorption maximum was situated at 342 nanometers with an absorption coefficient $\epsilon$ of 16,666, which coefficient reduces to 1935 at 400 nanometers.

EXAMPLE 8

Similarly, (nitro 4 phenyl) - 2 thiophene may be obtained from

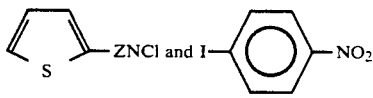

Its absorption maximum was at 344 nanometers with an absorption coefficient $\epsilon$ of 15,537. This coefficient reduces to 1624 at 400 nanometers.

Examples 5 to 8 how that excellent results can be obtained using a cyano attractor group (—CN) which is smaller than a nitro group (—$NO_2$).

The use of cyano derivatives turns out to be particularly advantageous in visible light since these products absorb this light much less than do the corresponding nitrate derivatives.

Naturally, the invention is not limited to the specific examples described, nor to the methods of synthesis mentioned.

We claim:

1. An organic material having non-linear optical properties, characterized by the fact that it satisfied one of the following formulas:

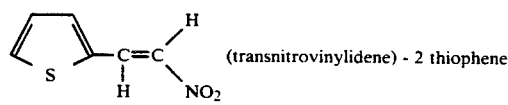

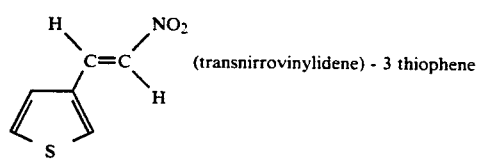

2. An organic material having non-linear optical properties, characterized by the fact that it satisfies one of the following formulas:

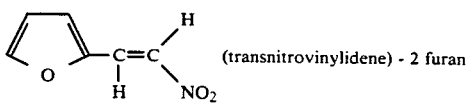

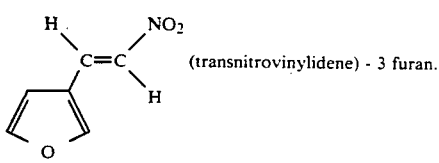

3. An organic material having non-linear optical properties, characterized by the fact that it satisfies the following formula:

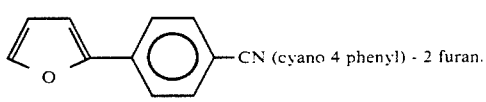 CN (cyano 4 phenyl) - 2 furan.

4. An organic material having non-linear properties, characterized by the fact that it satisfies the following formula:

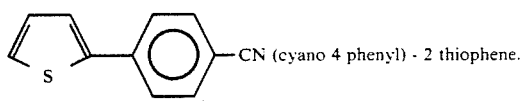 CN (cyano 4 phenyl) - 2 thiophene.

5. A method of preparing a material that satisfies the formula

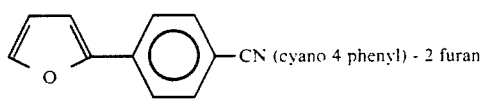 CN (cyano 4 phenyl) - 2 furan comprising coupling a zinc derivative having the formula

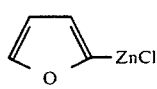

with para-bromobenzonitrile in the presence of catalytic quantities of palladium complexes.

6. A method of preparing a material that satisfies the formula

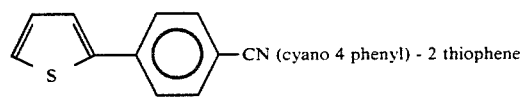 CN (cyano 4 phenyl) - 2 thiophene comprising coupling a magnesium derivative having the formula

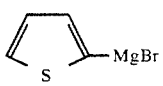

with para-iodobenzonitrile in the presence of catalytic quantities of palladium complexes.

7. A method of preparing a material that satisfies the formula

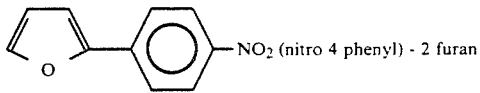 NO$_2$ (nitro 4 phenyl) - 2 furan comprising coupling a zinc derivative having the formula

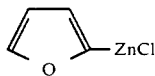

with para-iodonitrobenzene in the presence of catalytic quantities of palladium complexes.

8. A method of preparing a material that satisfies the formula

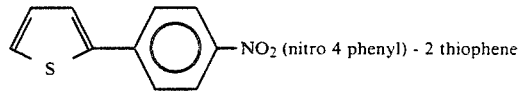 NO$_2$ (nitro 4 phenyl) - 2 thiophene comprising coupling a zinc derivative having the formula

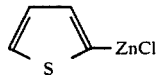

with para-iodonitrobenzene in the presence of catalytic quantities of palladium complexes.

* * * * *

UNITED STATES PATENT AND TRADEMARK OFFICE
CERTIFICATE OF CORRECTION

PATENT NO.  : 5,155,232

DATED       : October 13, 1992

INVENTOR(S) : Jean-Francois Fauvarque; Victorien Ratovelomanana;
              Anny Jutand; Christian Amatore It is certified that error appears in the above-identified patent and that said Letters Patent is hereby corrected as shown below:

Column 3, line 51, change "heteroaromatic cycle" to
          -- aromatic heterocycle --.

Column 6, line 4, change "ZNCl" to -- ZnCl --.
Column 6, line 18, change "ZNCl" to -- ZnCl --.
Column 6, line 47, change "transnirrovinylidene" to
          -- transnitrovinylidene --.

Signed and Sealed this

Eighth Day of February, 1994

Attest:

BRUCE LEHMAN

Attesting Officer           Commissioner of Patents and Trademarks